United States Patent [19]

Havera et al.

[11] Patent Number: 4,766,074
[45] Date of Patent: Aug. 23, 1988

[54] THERMOSTABLE RHIZOMUCOR RENNET HAVING INCREASED MILK CLOTTING ACTIVITY

[75] Inventors: Herbert J. Havera, Edwardsburg, Mich.; John D. Humphreys, Elkhart, Ind.

[73] Assignee: Miles Inc., Elkhart, Ind.

[21] Appl. No.: 107,776

[22] Filed: Oct. 13, 1987

Related U.S. Application Data

[63] Continuation of Ser. No. 819,720, Jan. 17, 1986, Pat. No. 4,722,900.

[51] Int. Cl.$^4$ .......................... C12N 9/58; C12R 1/785
[52] U.S. Cl. ...................................... 435/223; 435/931
[58] Field of Search ........................................ 435/223

[56] References Cited

U.S. PATENT DOCUMENTS

| | | |
|---|---|---|
| 4,348,482 | 9/1982 | Cornelius .............................. 435/223 |
| 4,362,818 | 12/1982 | Cornelius et al. ................... 435/223 |
| 4,530,906 | 7/1985 | Higashi et al. ....................... 435/223 |

FOREIGN PATENT DOCUMENTS 1185186  8/1986  Japan .................................. 435/223

*Primary Examiner*—Lionel M. Shapiro
*Attorney, Agent, or Firm*—Jerome L. Jeffers

[57] ABSTRACT

Disclosed is a method for increasing the milk clotting ability and reducing the thermal stability of microbial rennet from *Rhizomucor pusillus*. The method involves treating the rennet with a methionine oxidizing composition and the anhydride of a dicarboxylic organic acid.

12 Claims, 1 Drawing Sheet

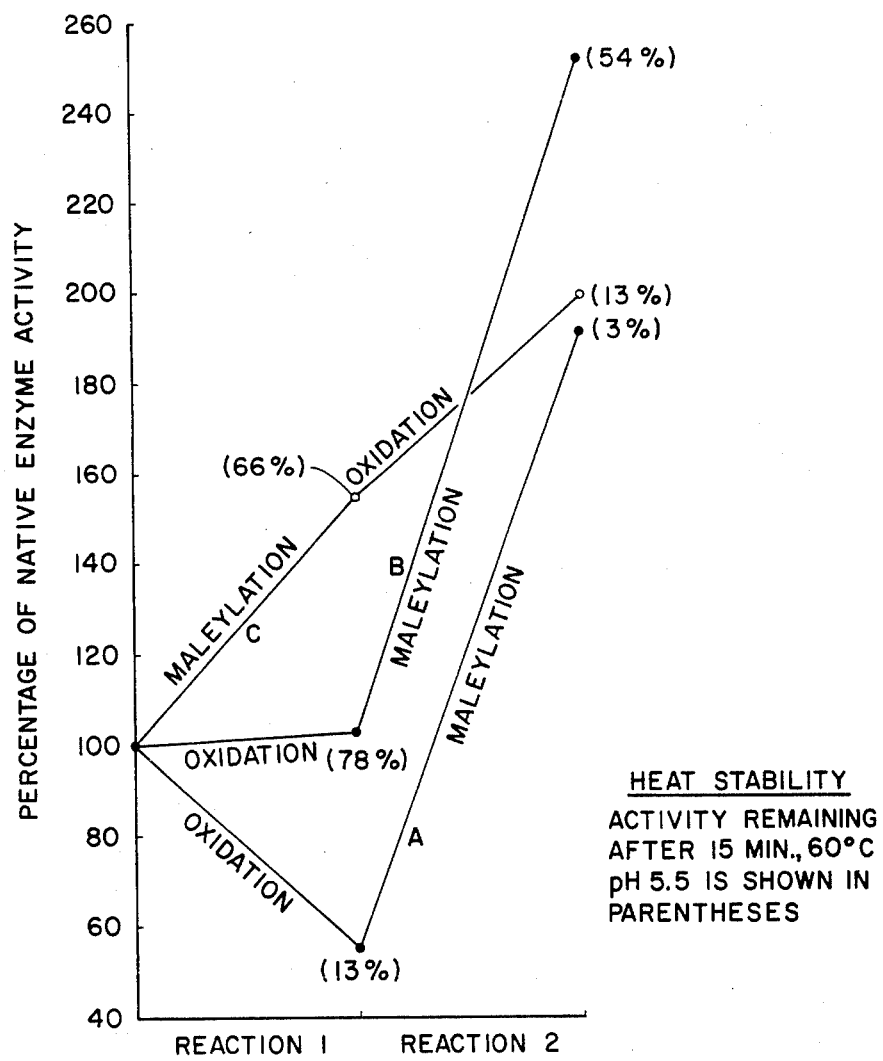

THERMOSTABLE RHIZOMUCOR RENNET HAVING INCREASED MILK CLOTTING ACTIVITY

This is a continuation, of application Ser. No. 819,720, filed Jan. 17, 1986, now U.S. Pat. No. 4,722,900.

BACKGROUND OF THE INVENTION

Calf rennet, obtained from the fourth stomach of unweaned calves, has traditionally been used as the coagulant for milk in the production of cheese. More recently, an enzyme produced during the fermentation of certain fungi has been found to be a suitable replacement for calf rennet, the supply of which is limited by the availability of calf stomachs.

While the milk clotting enzyme obtained from fungi (typically referred to as microbial rennet) is quite suitable for making cheese, it has a higher degree of thermal stability than calf rennet. This property is disadvantageous because the rennet ends up in the whey during the cheese making process, and residual rennet activity in the whey is undesirable. This presents no difficulty when calf rennet is used because it is thermally deactivated at normal pasteurization temperatures. This is not the case, however, with microbial rennet because of its greater thermal stability. Cornelius reports in U.S. Pat. No. 4,348,482 that the thermal stability of microbial rennet can be decreased without substantially reducing its milk clotting activity by contacting an aqueous solution thereof with a methionine-oxidizing means. This process has achieved significant acceptance in the marketplace, especially with microbial rennet from the fungus of the species *Rhizomucor miehei* (formerly *Mucor miehei*). The taxonomy of the genus Mucor was revised and both *Mucor pusillus* and *Mucor meihei* were reclassified into a new genus Rhizomucor because they were sufficiently different from other members of the genus Mucor to justify such reclassification.

Cornelius also reports in U.S. Pat. No. 4,362,818 that the milk coagulating activity of the microbial enzyme obtained from *R. pusillus* can be increased by acylating the enzyme with selected acid anhydrides, including maleic anhydride. This acylation typically results in an increase of about 50% in the enzyme's activity although in one run there is reported a product having 221% of its original activity after treatment with maleic anhydride.

Higashi et al report in U.S. Pat. No. 4,530,906 that the coagulating activity of microbial rennet from *R. pusillus* can be increased by treating it with succinic anhydride and that they have reported a low proteolytic activity/milk coagulating activity index for the treated enzyme.

SUMMARY OF THE INVENTION

The present invention is a method for increasing the milk coagulating activity and reducing the thermal stability of microbial rennet obtained from *Rhizomucor pusillus*. The method involves:

(a) contacting the rennet with a methionine-oxidizing composition under conditions suitable for and for a time sufficient to oxidize at least a portion of the methionine residues of the rennet to methionine sulfoxide; and (b) contacting the rennet with the anhydride of a dicarboxylic organic acid under conditions suitable for and for a time sufficient to increase its milk clotting activity.

Also included within the scope of this invention is the microbial rennet prepared by the process set out above.

DESCRIPTION OF THE INVENTION

The present invention provides a method for increasing the milk clotting activity and decreasing the thermal stability of *R. pusillus* rennet by oxidizing the enzyme with a methionine oxidizing agent followed by acylation with a dicarboxylic acid anhydride.

*R. pusillus* rennet is produced by well established methods and is commercially available as an aqueous solution. The native coagulant is more heat stable than calf rennet and to produce a heat labile preparation, processes have been developed to chemically modify the enzyme. These processes utilize methionine oxidizing agents such as hydrogen peroxide, peroxyacids and alkali metal hypochlorites which oxidize some of the methionine residues in the enzyme to methionine sulfoxide. By varying the extent of this oxidation a greater or lesser degree of thermal lability can be produced. Unfortunately, this treatment often produces a decrease in milk clotting activity and some compromise has to be established between the degree of thermal lability and the loss of clotting activity. Acylation of thermally destabilized rennet with a dicarboxylic acid anhydride as described herein provides a means to avoid this situation and permits the preparation of extremely labile rennets (if so desired) which have greatly increased milk clotting activity as compared to rennets that are oxidized to decrease their thermal stability but not acylated.

The oxidation conditions are not narrowly critical; the process may be carried out using any of a number of oxidizing agents which oxidize methionine such as hydrogen peroxide, other organic peroxides, peroxyacids, e.g. peracetic acid and persulfuric acid, chlorine containing oxidizing agents, e.g. sodium hypochlorite and chloramine-T (sodium salt of N-chloro-p-toluenesulfonamide). Oxidation temperatures will typically range from about 0° to 40° C. since at below 0° C. the enzyme solution will tend to freeze and the enzyme may undergo some inactivation at temperatures above 40° C. The oxidation is preferably carried out at a temperature in the range of from about 5° to 15° C. and is typically carried out at a pH in the range of 3 to 8 with a range of from about 4 to 6 being preferred. The oxidation is carried out for a period of time and with a concentration of oxidizing agent sufficient to provide the desired degree of thermal lability. The exact conditions required to achieve the desired degree of thermal destabilization will require some routine experimentation which can be conducted as follows:

Thermal Stability

The extent of destabilization of the enzyme may be determined as follows:

The enzyme is diluted in 0.2M phosphate buffer, pH 5.5 and aliquots (2 ml) are dispensed into screw cap test tubes. The tubes are placed in a water bath at 60° C. and then removed after 5, 10, 15 or 20 minutes, cooled in ice-water and assayed for residual milk-clotting activity as described below. An unheated sample of enzyme is used as a control (100% activity).

Milk Clotting Activity

Calcium chloride is added to homogenized whole milk to a final concentration of 3 mM. Aliquots (1 mL) of this solution are dispensed into test tubes and equilibrated in a water bath at 37° C. A sample (0.1 mL) of enzyme at a suitable dilution is then added, the solution rapidly mixed and the time to the first appearance of clotting measured. By comparing this time to the clotting time of a standard rennet solution (50 Rennet Units per mL, supplied by Marschall Products Division of Miles Laboratories, Inc., Madison, Wis.), the clotting activity may be calculated using the following formula:

Clotting Activity (Rennet Units/mL) =

$$\frac{\text{Clotting time of Std. (sec.)}}{\text{Dilution of Standard}} \times \frac{\text{Dilution of Test}}{\text{Clotting Time of Test (sec.)}} \times 50$$

Rennet activity is expressed in Rennet Units (R.U.) per milliliter when the enzyme is in a liquid form. Commercial rennets are usually supplied as "single strength" (90 R.U./mL) or "double strength" (180 R.U./mL).

The acylation reaction may be carried out with any suitable dicarboxylic acid anhydride. Typically an acid anhydride characterized by one of the following formulae is used:

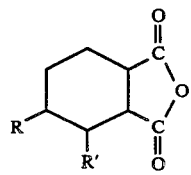

(a)

where R is $CO_2H$ or H, R' is $NO_2$ or H and the ring is saturated or unsaturated;

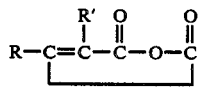

(b)

where R is Cl, Br, H or $CH_3$ and R' is H or Cl; or

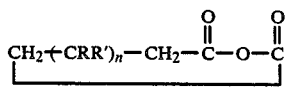

(c)

where n is 0 or 1 and R and R' are $CH_3$ when n is 1.

The acylation is carried out at a temperature in the range of from about 0° to 40° C. preferably from 5° to 25° C. The pH of the reaction medium is typically maintained in the range of from 5 to 10 with a pH of from 6 to 8 being preferred. A range of anhydride concentration from about 0.1 to 2 percent (w/v anhydride to enzyme solution) is used with single strength rennet (90 Rennet Units per mL) or its equivalent. The degree of increase in milk clotting activity is dependent upon the above factors and on the nature of the anhydride used. Optimum reaction conditions may be determined by varying these parameters and monitoring the reaction using the tests described above.

Since the process of the present invention involves two steps, it can be carried out either with the oxidation or acylation step first. The figure illustrates the effect of varying the reaction order. Referring to the drawing, line A represents acylation of a sample which was highly oxidized. Its heat stability was low (13% activity retained after 15 minutes at 60°, pH 5.5) and it had lost almost half of its original activity. Maleylation increased the activity to almost twice that of the native enzyme but thermal stability declined even further (3% activity retained). By comparison, calf rennet retains 56% activity after heating under these conditions. Line B represents a sample that was oxidized for only 5 hours with 1% hydrogen peroxide, pH 5.5, 4° C. Its activity did not change and its heat stability was the same as the native enzyme (78% activity retained). However, when it was maleylated the activity rose to 2½ times that of the native enzyme and the heat stability decreased to that of calf rennet (54% activity retained). It appears preferable to oxidize the enzyme and then perform the acylation because pursuant to this embodiment either the maximum activity is realized (250%-vs-200% for the reverse reaction) without unduly destabilizing the enzyme (limited oxidation) or an extremely thermolabile enzyme is produced without losing too much activity (extensive oxidation). The reverse reaction seems to produce products which have characteristics intermediate between these extremes and thus is less desirable. It is desirable to have a thermal stability similar to that of calf rennet since whey pasteurization conditions have been tailored to the destruction of this enzyme. A less stable enzyme would also be destroyed, of course, but this could lead to stability problems during long term storage. Thus, in a preferred embodiment the enzyme is contacted with $H_2O_2$ at a temperature of from about 5° to 15° and at a pH of from about 4 to 6 for a time sufficient to oxidize it to an extent such that the heat stability of the final product after acylation is decreased to a level whereby it retains 50 to 60% of its milk clotting activity when heated to 60° C. at pH 5.5 for 15 minutes and then acylated. Line C represents the reverse reaction order. The sample was first maleylated; its activity rose by 55% and its thermal stability decreased slightly. Surprisingly, when this sample was oxidized for 3 hours with 1% hydrogen peroxide, pH 5.5, 4° C., its activity increased before starting to fall again. The heat stability of th sample with the maximum activity was a little low (13% activity retained). These examples demonstrate that not only is the order in which the reactions are performed important but by changing the order and conditions a range of products with increased activity and varied thermal stability can be made. More specifically for maximum activity it is desirable to oxidize for a short time and then acylate but for minimum thermal stability it is desirable to oxidize to a greater degree, which results in some loss of enzyme activity, and then acylate to increase the activity.

The method of practicing the invention is further illustrated by th following examples.

EXAMPLE I

Microbial rennet from *R. pusillus* was oxidized as follows:

Hydrogen peroxide was added to the rennet to a final concentration of 1% (w/v) at pH 5.5, 4° C. Samples were removed at intervals and tested for heat stability as disclosed above. When the heat stability had reached the desired level (after approximately 5 days) the reaction was terminated by the addition of catalase to destroy any remaining hydrogen peroxide. This extensive modification resulted in the loss of over 50% of the enzyme activity before any acylation was carried out.

EXAMPLE II

In this and subsequent examples, the rennet used was oxidized as in Example I unless otherwise stated.

To 20 ml of oxidized *R. pusillus* rennet was added 100 mg (1 m mole) of maleic anhydride with stirring at room temperature. Several runs were conducted with the pH adjusted to various levels ranging from 6.5 to 9.0 with 1N NaOH. The NaOH was added with stirring which was discontinued upon completion of the NaOH addition. After the reaction was complete, the pH of the reaction mixture was adjusted to 5.5 with 1N HCl since the enzyme is more stable at this pH.

The milk coagulating activities of the acylated, oxidized enzymes were determined and compared with the milk coagulating activity of the oxidized enzyme (which had not been acylated) used as a control. The results of maleylation at different pHs are summarized in Table I.

TABLE I

Reaction of Oxidized *R. pusillus* Microbial Rennet Enzyme with Maleic Anhydride at Different pHs (6.5–9.0)

| pH | Activity (R.U./ml) | Final Vol. (ml) | Total Act. (R.U.) | Percent of Original |
|---|---|---|---|---|
| Control | 50.9 | 20 | 1019 | 100 |
| 6.5 | 130.3 | 22.6 | 2944 | 288 |
| 7.0 | 138.0 | 22.5 | 3105 | 304 |
| 7.5 | 144.7 | 22.6 | 3273 | 321 |
| 8.0 | 146.5 | 22.6 | 3315 | 325 |
| 8.5 | 140.0 | 22.6 | 3169 | 310 |
| 9.0 | 134.4 | 22.7 | 3052 | 299 |

EXAMPLE III

To 20 ml of oxidized *R. pusillus* rennet there was added various amounts of maleic anhydride (50 mg–200 mg, 0.5 m mole–2 m mole) with stirring at room temperature while keeping the pH at 7.5 with 1N NaOH. Stirring was carried out during the addition of the NaOH solution. After the maleyation was complete, the pH of the reaction mixture was adjusted to 5.5 with 1N HCl.

The milk coagulating activities of the acylated oxidized enzymes were determined and compared with the milk coagulating activity of the oxidized enzyme which was used as a control. The results of acylation with varying amounts of maleic anhydride are summarized in Table II.

TABLE II

Reaction of Oxidized *R. pusillus* Microbial Rennet Enzyme with Different Amounts of Maleic Anhydride (at pH 7.5)

| Amount of Maleic Anhydride (mg) | Activity (R.U./ml) | Final Vol. (ml) | Total Act. (R.U.) | Percent of Original |
|---|---|---|---|---|
| Control (0) | 50.9 | 20 | 1019 | 100 |
| 50 | 104.8 | 21.7 | 2279 | 223 |
| 100 | 144.7 | 22.6 | 3273 | 321 |
| 150 | 120.2 | 23.3 | 2797 | 274 |
| 200 | 87.4 | 24.1 | 2104 | 206 |

From the above data it can be determined that an activity maximum is reached with continued addition of the anhydride.

EXAMPLE IV

To 20 ml of oxidized *R. pusillus* rennet was added 100 mg (1 m mole) of maleic anhydride with stirring at various temperatures (4°, 22° and 37° C.) while keeping the pH at 7.5 with 1 N NaOH. Stirring was continued during the NaOH addition during which time the maleylation reation took place and then the pH of the reaction mixture was adjusted to 5.5 with 1 N HCl.

The milk coagulating activities of the acylated oxidized enzymes were determined and compared with the milk coagulating enzyme used as control. The results of maleylation at different temperatures are summarized in Table III.

TABLE III

Reaction of Oxidized *R. pusillus* Microbial Rennet Enzyme with Maleic Anhydride at pH 7.5 at Different Temperatures

| Temperature | Activity (R.U./ml) | Final Vol. (ml) | Total Act. (R.U.) | Percent of Original |
|---|---|---|---|---|
| Control | 43.0 | 20 | 860 | 100 |
| 4° C. | 134.7 | 23.5 | 3165 | 367 |
| 22° C. | 128.0 | 23.6 | 3035 | 352 |
| 37° C. | 116.6 | 23.6 | 2754 | 319 |

EXAMPLE V

To 20 ml of oxidized *R. pusillus* rennet was added 1 m mole of the various anhydrides set out in Table IV. In each case sodium hydroxide was added, with stirring, as needed to maintain the pH at 7.5. The reaction was considered complete when no additional NaOH was needed to keep the pH at 7.5. This took from 30–45 minutes depending on the particular anhydride being used. After the reaction was complete, the pH of the reaction mixture was adjusted to 5.5 with 1 N HCl.

The milk coagulating activities of the acylated oxidized enzymes were determined and compared with the milk coagulating activity of the oxidized enzyme used as a control. The results of acylation of the oxidized *R. pusillus* with various anhydrides are summarized in Table IV.

TABLE IV

Reaction of Oxidized *R. pusillus* Microbial Rennet Enzyme with Various Anhydrides at Room Temperature at pH 7.5

| Anhydride | Activity (R.U./ml) | Final Vol. (ml) | Total Act. (R.U.) | Percent of Original |
|---|---|---|---|---|
| Control | 44 | 20 | 880 | 100 |
| Maleic | 125–145* | 23.3 | 2912–3378 | 330–383 |
| Succinic | 78 | 23.5 | 1826 | 207 |
| Dichloromaleic | 125 | 23.3 | 2908 | 330 |
| Citraconic | 75 | 23.3 | 1742 | 213 |
| Phthalic | 123 | 23.0 | 2822 | 345 |
| Homophthalic | 37 | 23.3 | 868 | 100 |
| 3-Nitrophthalic | 39 | 23.4 | 900 | 102 |
| Bromomaleic | 107 | 23.3 | 2500 | 330 |
| 1,2,4,benzene tricarboxylic | 95 | 24.1 | 2300 | 278 |
| cis 1,2 cyclohexane dicarboxylic | 117 | 23.5 | 2750 | 333 |
| 3,3 dimethyl glutaric | 61 | 23.0 | 1410 | 164 |

*5 runs were made.

EXAMPLE VI

R. pusillus rennet was oxidized with a 1% $H_2O_2$ solution at 4° C. for 6 hours after which time the heat stability of the enzyme was still the same as the native enzyme and no activity had been lost. Twenty ml samples were removed every hour for maleylation using the procedure described in Example V.

The milk coagulating activities of the acylated oxidized enzymes were determined and compared with the milk coagulating activity of the oxidized enzyme used as control. The results of this limited oxidation and acylation on the activity of the enzyme are summarized in Table V.

TABLE V
Effect of Limited Oxidation Followed by Maleylation on Clotting Activity

| Time | Activity (R.U.(m/l) | Final Vol. (ml) | Total Act. (R.U.) | Percent of Original |
|---|---|---|---|---|
| 0 Hr. (Control) | 92.2 | 20 | 1826 | 100 |
| 1 Hr. Oxidized | 88.6 | 20 | 1755 | 96.1 |
| 1 Hr. Maleylated | 174 | 23.23 | 4055 | 222 |
| 2 Hr. Oxidized | 87.7 | 20 | 1772 | 97.1 |
| 2 Hr. Maleylated | 166 | 23.18 | 3849 | 211 |
| 3 Hr. Oxidized | 93.5 | 20 | 1852 | 102 |
| 3 Hr. Maleylated | 173.2 | 23.1 | 4002 | 229 |
| 4 Hr. Oxidized | 94.6 | 20 | 1891 | 104 |
| 4 Hr. Maleylated | 196 | 23.3 | 4574 | 250 |
| 5 Hr. Oxidized | 94.7 | 20 | 1895 | 104 |
| 5 Hr. Maleylated | 197 | 23.4 | 4602 | 252 |
| 6 Hr. Oxidized | 94.9 | 20 | 1898 | 104 |
| 6 Hr. Maleylated | 195.4 | 23.8 | 4644 | 254 |

From the data of Table V it can be determined that even very limited oxidation potentiates the effect of maleic anhydride, resulting in higher activity than could be produced by the anhydride alone.

EXAMPLE VII

R. pusillus rennet was maleylated as described in Example V. To a 20 ml sample of the maleylated enzyme was added 0.4 ml of 50% (w/v) hydrogen peroxide solution (to give a final concentration of 1% w/v) at pH 5.6 at 4° C. with stirring. The solution was maintained at 4° C. and samples were removed at intervals for assay. The results of this experiment are set out in Table VI.

TABLE VI
Effect of Oxidation of Maleylated R. pusillus Rennet

| Time (Hrs.) | Activity (R.U./ml) | Final Vol. (ml) | Total Act. (R.U.) | Percent of Original |
|---|---|---|---|---|
| 0 (Control) | 141.5 | 20 | 2830 | 100 |
| 2 | 156.8 | 20.4 | 3199 | 113 |
| 3 | 178.3 | 20.4 | 3637 | 129 |
| 4 | 176.1 | 20.4 | 3592 | 127 |

Heat stability (activity remaining after 15 minutes, 60° C., pH 5.5); Native R. pusillus rennet—80%; Maleylated R. pusillus rennet—66%; Oxidized (3 hrs.) maleylated R. pusillus rennet—13%.

What is claimed is:

1. Microbial rennet obtained from an organism of the species Rhizomucor pusillus and having enhanced milk clotting activity which is prepared by:
   (a) providing a solution of rennet obtained from Rhizomucor pusillus;
   (b) contacting the rennet with a methionine oxidizing composition under conditions suitable and for a time sufficient to increase the thermal liability of the rennet; and
   (c) contacting the rennet with the anhydride of a dicarboxylic organic acid under conditions suitable and for a time sufficient to increase its milk clotting activity.

2. The rennet of claim 1 wherein the oxidizing composition is $H_2O_2$.

3. The rennet of claim 1 wherein the oxidation is carried out at a temperature of from about 5° to 15° C. and at a pH of from about 4 to 6.

4. The method of claim 1 wherein the acid anhydride is characterized by the formula:

(a) [cyclohexane ring structure with carboxylic anhydride group, R substituent, and R' substituent]

where R is $CO_2H$ or H, R' is $NO_2$ or H and the ring is saturated or unsaturated;

$$R-C=C-C-O-C \quad (b)$$
with R' on the second C, and carbonyl groups where R is Cl, Br, H or $CH_3$ and R' is H or Cl; or $$CH_2\text{-}(CRR')_n\text{-}CH_2\text{-}C\text{-}O\text{-}C \quad (c)$$

where n is 0 or 1 and R and R' are $CH_3$ when n is 1.

5. The rennet of claim 1 wherein the acylation is carried out at a temperature in the range of from about 0° to 40° C.

6. The rennet of claim 5 wherein the temperature is from 5° to 25° C.

7. The rennet of claim 1 wherein the pH is maintained in the range of from 5 to 10 during the acylation.

8. The rennet of claim 5 wherein the pH is from 6 to 8.

9. The rennet of claim 1 wherein the acid anhydride concentration is from about 0.1 to 2 percent (w/v) anhydride to rennet solution based on a rennet solution having a strength of 90 Rennet Units per mL.

10. The rennet of claim 1 wherein the oxidation step is carried out before the treatment with the acid anhydride.

11. The rennet of claim 10 wherein it is oxidized and then the solution is treated with maleic anhydride to increase the rennet's milk clotting activity such that the resulting product retains about 50 to 60% of its milk clotting activity when heated to 60° C. at pH 5.5 for 15 minutes.

12. Microbial rennet having enhanced milk clotting activity prepared by:
   (a) providing a solution of rennet obtained from an organism of the species Rhizomucor pusillus;
   (b) first contacting the rennet with $H_2O_2$ at a temperature of from about 5° to 15° C. and at a pH of from about 4 to 6 for a time sufficient to oxidize the rennet to an extent such that the heat stability of the final product after acylation is decreased to a level whereby it retains 50 to 60% of its milk clotting activity when heated to 60° C. at pH 5.5 for 15 minutes; and then (c) contacting the rennet with maleic anhydride at a temperature of from 0° to 40° C. and a pH of from 5 to 10 with a meleic anhydride concentration of from about 0.1 to 2 percent (w/v anhydride to rennet solution) based on an enzyme solution having a strength of 90 Rennet Units per mL for a time sufficient to increase the milk clotting activity of the rennet to a level which is higher than could be achieved by treating it with meleic anhydride in the absence of oxidation.

* * * * *